US012660982B2

(12) United States Patent
Barbato et al.

(10) Patent No.: US 12,660,982 B2
(45) Date of Patent: Jun. 23, 2026

(54) MEDICAL IMAGING SYSTEMS, DEVICES, AND RELATED METHODS OF USE

(71) Applicant: Boston Scientific Scimed, Inc., Maple Grove, MN (US)

(72) Inventors: Louis J. Barbato, Franklin, MA (US); Kirsten Viering, Newton, MA (US); Amy Levasseur, Holliston, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 81 days.

(21) Appl. No.: 18/519,383

(22) Filed: Nov. 27, 2023

(65) Prior Publication Data

US 2024/0172918 A1 May 30, 2024

Related U.S. Application Data

(60) Provisional application No. 63/428,779, filed on Nov. 30, 2022.

(51) Int. Cl.
| | |
|---|---|
| *A61B 1/00* | (2006.01) |
| *H04N 7/18* | (2006.01) |
| *H04N 23/62* | (2023.01) |

(52) U.S. Cl.
CPC ........ *A61B 1/00009* (2013.01); *A61B 1/0004* (2022.02); *A61B 1/00048* (2013.01);
(Continued)

(58) Field of Classification Search
CPC .............. A61B 1/00009; A61B 1/0004; A61B 1/00048; A61B 1/00124; A61B 1/00052;
(Continued)

(56) References Cited

U.S. PATENT DOCUMENTS

| | | |
|---|---|---|
| 8,827,899 B2 | 9/2014 | Farr et al. |
| 11,389,064 B2 | 7/2022 | Sanchez et al. |

(Continued)

FOREIGN PATENT DOCUMENTS

| | | |
|---|---|---|
| WO | 2014041503 A1 | 3/2014 |
| WO | 2016007276 A1 | 1/2016 |
| WO | 2021165363 A1 | 8/2021 |

OTHER PUBLICATIONS

International Search Report and Written Opinion in International Application No. PCT/US2023/081083, dated Feb. 6, 2024 (9 pages).

*Primary Examiner* — Asmamaw G Tarko
(74) *Attorney, Agent, or Firm* — Bookoff McAndrews, PLLC

(57) ABSTRACT

A portable computing device of a medical imaging system that is connectable to a controller includes: a medical device connector for connecting a medical device that includes an imaging device to the computing device, at least one memory storing instructions, and one or more processors including an image processor. Execution of the instructions by the processors cause the computing device to perform operations, including to determine a connection status of the computing device and the controller, operate the computing device in a first or second operating mode based on the connection status, and receive image signals from the imaging device. When the computing device is operating in the first operating mode, the image signals are processed, by the image processor, to generate image data. When the computing device is operating in the second operating mode, the image signals are provided to the controller for processing.

20 Claims, 9 Drawing Sheets

(52) U.S. Cl.
CPC ......... *A61B 1/00124* (2013.01); *H04N 7/183* (2013.01); *H04N 23/62* (2023.01)

(58) Field of Classification Search
CPC .... A61B 1/00006; H04N 7/183; H04N 23/62; G06F 1/1632; G06F 3/1423; G06F 3/147; G16H 30/20; G16H 40/63
USPC .......................................................... 348/65
See application file for complete search history.

(56) References Cited

U.S. PATENT DOCUMENTS

| | | | |
|---|---|---|---|
| 2008/0200758 A1* | 8/2008 | Orbay | A61B 1/00105 600/170 |
| 2012/0162401 A1 | 6/2012 | Melder et al. | |
| 2015/0150440 A1* | 6/2015 | Salvati | A61B 1/32 600/109 |
| 2016/0000300 A1* | 1/2016 | Williams | A61B 1/05 600/109 |
| 2017/0242240 A1* | 8/2017 | Krivopisk | A61B 1/00188 |
| 2018/0070797 A1* | 3/2018 | Fujita | A61B 1/045 |
| 2018/0177382 A1* | 6/2018 | Yagi | H04N 23/632 |
| 2019/0350440 A1* | 11/2019 | Leong | A61B 1/0052 |
| 2020/0060537 A1* | 2/2020 | Rephaeli | G02B 23/2423 |
| 2021/0369366 A1* | 12/2021 | Hwang | A61B 1/00011 |
| 2022/0283770 A1* | 9/2022 | Chung | G06F 3/042 |
| 2023/0154580 A1* | 5/2023 | Wang | G16H 50/20 382/118 |
| 2023/0363834 A1* | 11/2023 | Diaz-Chiosa | A61B 34/37 |
| 2024/0065531 A1* | 2/2024 | Ouyang | A61B 1/00097 |

* cited by examiner

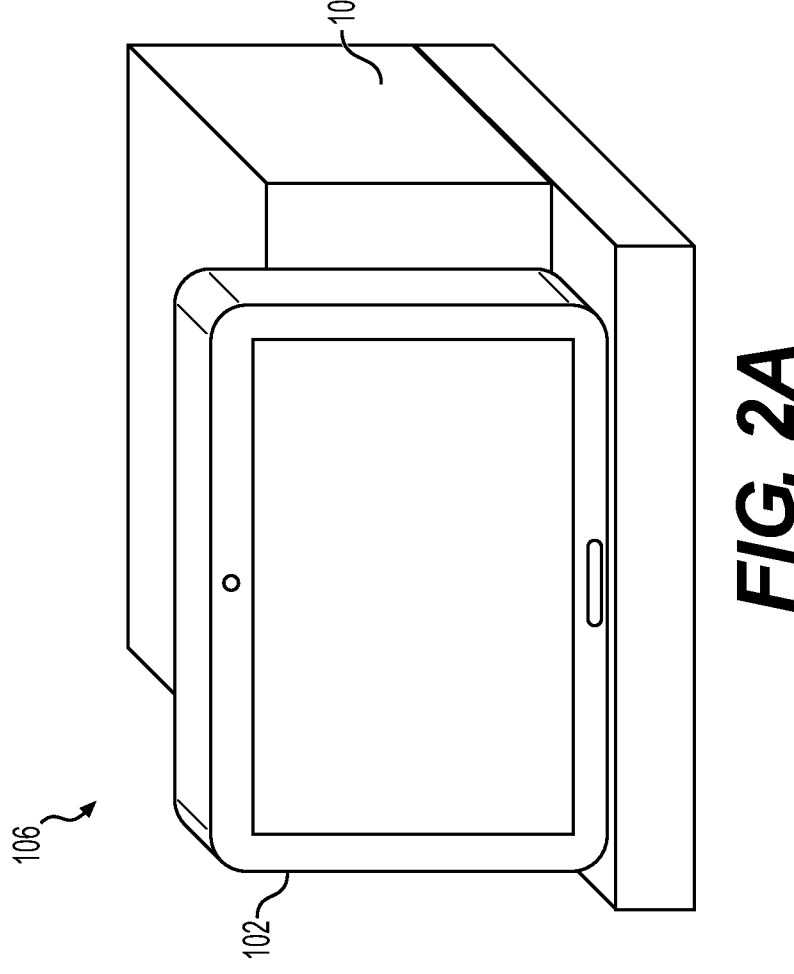
*FIG. 2A*

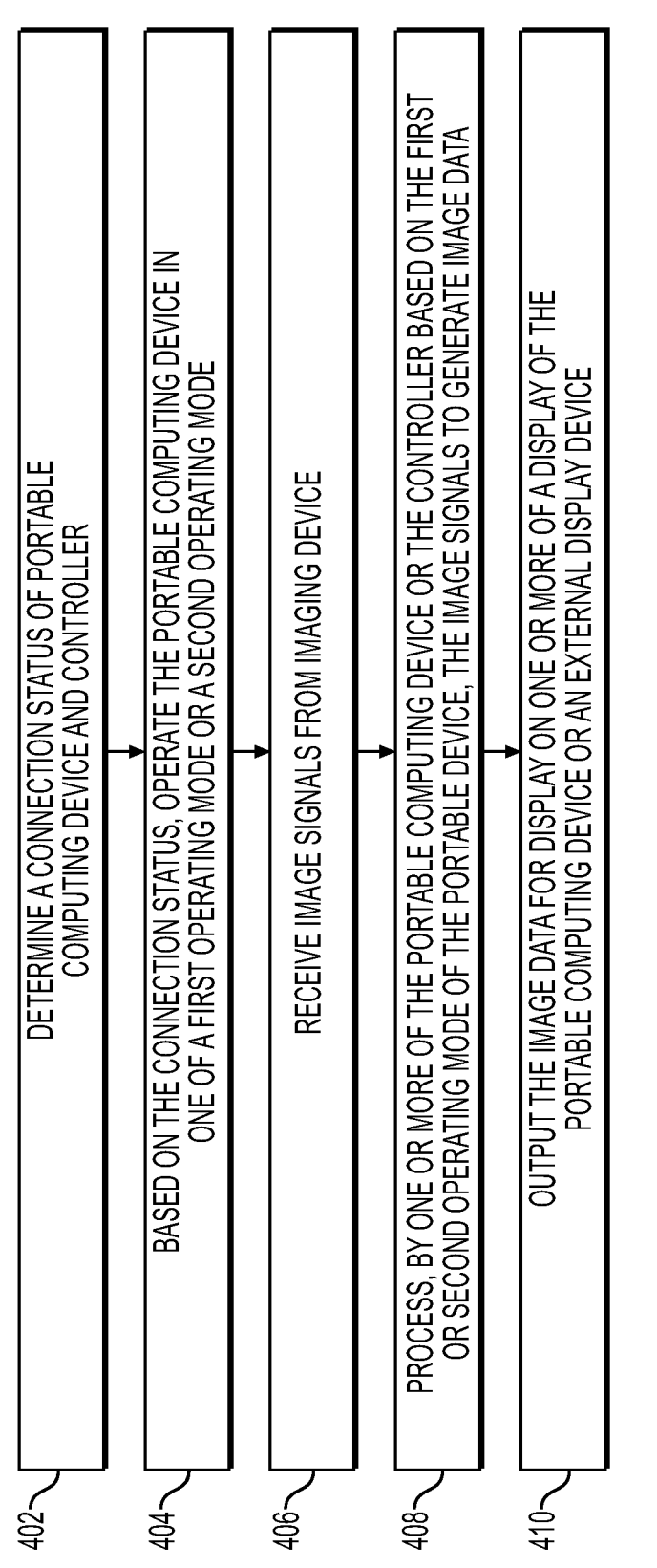

400

402 — DETERMINE A CONNECTION STATUS OF PORTABLE COMPUTING DEVICE AND CONTROLLER

404 — BASED ON THE CONNECTION STATUS, OPERATE THE PORTABLE COMPUTING DEVICE IN ONE OF A FIRST OPERATING MODE OR A SECOND OPERATING MODE

406 — RECEIVE IMAGE SIGNALS FROM IMAGING DEVICE

408 — PROCESS, BY ONE OR MORE OF THE PORTABLE COMPUTING DEVICE OR THE CONTROLLER BASED ON THE FIRST OR SECOND OPERATING MODE OF THE PORTABLE DEVICE, THE IMAGE SIGNALS TO GENERATE IMAGE DATA

410 — OUTPUT THE IMAGE DATA FOR DISPLAY ON ONE OR MORE OF A DISPLAY OF THE PORTABLE COMPUTING DEVICE OR AN EXTERNAL DISPLAY DEVICE

*FIG. 4*

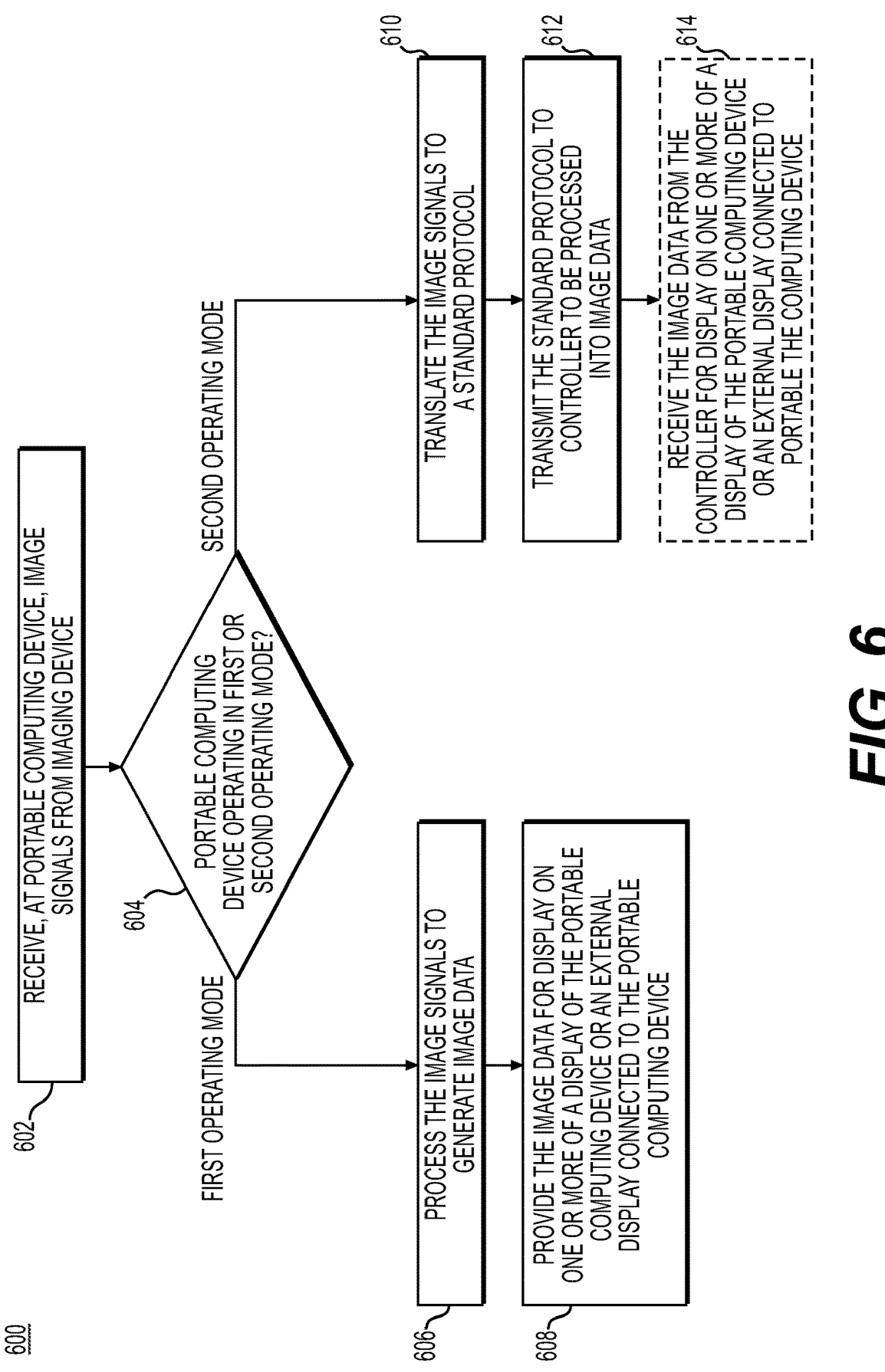

602 — RECEIVE, AT PORTABLE COMPUTING DEVICE, IMAGE SIGNALS FROM IMAGING DEVICE

604 — PORTABLE COMPUTING DEVICE OPERATING IN FIRST OR SECOND OPERATING MODE?

FIRST OPERATING MODE

606 — PROCESS THE IMAGE SIGNALS TO GENERATE IMAGE DATA

608 — PROVIDE THE IMAGE DATA FOR DISPLAY ON ONE OR MORE OF A DISPLAY OF THE PORTABLE COMPUTING DEVICE OR AN EXTERNAL DISPLAY CONNECTED TO THE PORTABLE COMPUTING DEVICE

SECOND OPERATING MODE

610 — TRANSLATE THE IMAGE SIGNALS TO A STANDARD PROTOCOL

612 — TRANSMIT THE STANDARD PROTOCOL TO CONTROLLER TO BE PROCESSED INTO IMAGE DATA

614 — RECEIVE THE IMAGE DATA FROM THE CONTROLLER FOR DISPLAY ON ONE OR MORE OF A DISPLAY OF THE PORTABLE COMPUTING DEVICE OR AN EXTERNAL DISPLAY CONNECTED TO PORTABLE THE COMPUTING DEVICE

MEDICAL IMAGING SYSTEMS, DEVICES, AND RELATED METHODS OF USE

CROSS-REFERENCE TO RELATED APPLICATIONS

This application claims the benefit of priority from U.S. Provisional Application No. 63/428,779, filed Nov. 30, 2022, which is incorporated by reference herein in its entirety.

TECHNICAL FIELD

The disclosure relates generally to medical imaging systems, devices, and related methods of use. More specifically, aspects of the disclosure pertain to medical imaging systems including portable computing devices that are detachable and independently operable from controllers to perform image processing to accommodate implementation across various clinical settings.

BACKGROUND

Medical procedures performed to image a body lumen of a patient using an endoscopic imaging system are often performed in one of two clinical settings. In a first clinical setting, the procedure may be performed in a dedicated area or room, such as an endoscopy suite. In a second clinical setting, the procedure may be performed bedside (e.g., if the procedure is emergent or if patient isolation may be required). The first and second clinical settings typically have different needs with respect to portability and/or size constraints of the endoscopic imaging system, as well as image processing capabilities of the endoscopic imaging system. Resultantly, two separate types of endoscopic imaging systems have conventionally been used in each setting.

For example, a mobile endoscopic imaging system, including a portable computing device (e.g., a tablet) to which an endoscope is connected, may be utilized for a bedside procedure. This system has high portability, consumes less space, and has quicker set up times, albeit with less advanced image processing capabilities. Alternatively, for a procedure performed in a dedicated area, a dedicated controller configured to perform advanced image processing may be utilized and connected to external display devices and/or other system interfaces to output image data.

SUMMARY

A portable computing device of a medical imaging system connectable to a controller may include a medical device connector for connecting a medical device to the portable computing device. The medical device may include an imaging device. The portable computing device may also include at least one memory storing instructions, and one or more processors, including an image processor, where execution of the instructions by the one or more processors, may cause the portable computing device to perform operations. The operations may include to determine a connection status of the portable computing device and the controller, and operate the portable computing device in a first operating mode or a second operating mode based on the connection status. The operations may also include to receive image signals from the imaging device. When the portable computing device is operating in the first operating mode, the image signals may be processed, by the image processor, to generate image data. When the portable computing device is operating in the second operating mode, the image signals may be provided to the controller for processing to generate the image data.

In any of the exemplary portable computing devices disclosed herein, to determine the connection status, a physical connection status of the portable computing device and the controller may be determined, and in response to determining there is a physical connection of the portable computing device and the controller based on the physical connection status, a communicative connection status of the portable computing device and the controller may be determined. When the physical connection status indicates there is no physical connection of the portable computing device and the controller, the portable computing device may be operated in the first operating mode. To determine the communicative connection status, a negotiation process may be initiated between the portable computing device and the controller to determine whether a communicative connectivity threshold is met. In response to determining that the communicative connectivity threshold is not met, the portable computing device may be operated in the first operating mode. Otherwise, in response to determining that the communicative connectivity threshold is met, the portable computing device may be operated in the second operating mode.

In some aspects, the connection status of the portable computing device and the controller may be periodically determined at predefined intervals. In other aspects, the connection status of the portable computing device and the controller may be determined in response to detecting a trigger event. At least one trigger event may include the receiving of the image signals from the imaging device.

In further aspects, when the portable computing device is operating in the first operating mode, the generated image data may be displayed on a display of the portable computing device and/or the generated image data may be provided for display on an external display device connected to the portable computing device. When the portable computing device is operating in the first operating mode, the portable computing device may provide a first user interface on a display of the portable computing device. The first user interface may include a subset of a plurality of imaging-related feature controls corresponding to subset of a plurality of operations that are enabled to be performed by the portable computing device. When the portable computing device is operating in the second operating mode, the portable computing device may provide a second user interface on the display of the portable computing device. The second user interface may include the plurality of imaging-related feature controls corresponding to the plurality of operations that are enabled to be performed by the controller.

In additional aspects, when the portable computing device is operating in the second operating mode and the image signals are provided to the controller for processing to generate the image data, the image signals may be translated to a standard protocol, and the standard protocol may be transmitted to the controller to be processed. An image processor of the controller may be configured to perform more advanced image processing than the image processor of the portable computing device. Additionally, when the portable computing device is operating in the second operating mode, the generated image data may be received from the controller for display on one or more of a display of the portable computing device or an external display device connected to the portable computing device.

In some aspects, the portable computing device may also include a connector receptacle configured to receive a connector of the controller to connect the portable computing device to the controller. In other aspects, the portable computing device may be configured to receive one or more connector cables that connect the portable computing device to the controller. The one or more connector cables may connect the portable computing device to the controller via a mount configured to receive the portable computing device.

A system for medical image processing may include a controller having a first image processor, and a portable computing device connectable to the controller. The portable computing device may include a medical device connector for connecting a medical device to the portable computing device. The medical device may include an imaging device. The portable computing device may also include at least one memory storing instructions, and one or more processors, including a second image processor, where execution of the instructions by the one or more processors, may cause the portable computing device to perform operations. The operations may include determining a connection status of the portable computing device and the controller, and operating the portable computing device in a first or second operating mode. The portable computing device may be operated in the first operating mode based on a negative connection status and operated in the second operating mode based on a positive connection status. The operations may also include receiving image signals from the imaging device. When the portable computing device is operating in the first operating mode, the image signals may be processed, by the second image processor, to generate image data. When the portable computing device is operating in the second operating mode, the image signals may be provided to the controller for processing, by the first image processor, to generate the image data.

In any of the systems disclosed herein, to provide the image signals to the controller for processing, the image signals may be translated to a standard protocol, and the standard protocol may be transmitted to the controller for processing by the first image processor to generate the image data. The first image processor of the controller may be configured to perform more advanced image processing than the second image processor of the portable computing device. In some aspects, the controller may be a docking station having a connector, and the portable computing device further includes a connector receptacle for receiving the connector to connect the portable computing device to the controller. In other aspects, the controller and a mount for the portable computing device may be mounted to a mobile stand, and one or more connector cables connect the portable computing device to the controller.

A method for medical image processing may include determining a connection status of a portable computing device having a first image processor and a controller having a second image processor, where an imaging device of a medical device may be connected to the portable computing device. The method may also include operating the portable computing device in a first or second operating mode based on the connection status. The portable computing device may be operated in the first operating mode based on a negative connection status and operated in the second operating mode based on a positive connection status. The method may further include receiving image signals from the imaging device. When the portable computing device is operating in the first operating mode, the image signals may be processed, by the first image processor, to generate image data. When the portable computing device is operating in the second operating mode, the image signals may be translated to a standard protocol, and the standard protocol may be transmitted to the controller for processing by the second image processor to generate the image data.

Any of the exemplary methods disclosed herein, for determining the connection status, may include determining a physical connection status of the portable computing device and the controller, and in response to determining there is a physical connection of the portable computing device and the controller based on the physical connection status, determining a communicative connection status of the portable computing device and the controller.

It may be understood that both the foregoing general description and the following detailed description are exemplary and explanatory only and are not restrictive of the invention, as claimed. As used herein, the terms "comprises," "comprising," "including," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." The term "distal" refers to a direction away from an operator/toward a treatment site, and the term "proximal" refers to a direction toward an operator. The term "approximately," or like terms (e.g., "substantially"), includes values+/−10% of a stated value.

BRIEF DESCRIPTION OF THE DRAWINGS

The accompanying drawings, which are incorporated in and constitute a part of this specification, illustrate examples of this disclosure and together with the description, serve to explain the principles of the disclosure.

FIGS. 2A and 2B depict a first configuration of a portable computing device and a controller of the medical imaging system of FIG. 1.

FIG. 4 depicts an exemplary process for processing image signals received from an imaging device.

FIG. 6 depicts an exemplary process for operating mode-dependent image processing.

DETAILED DESCRIPTION

Figure 1:
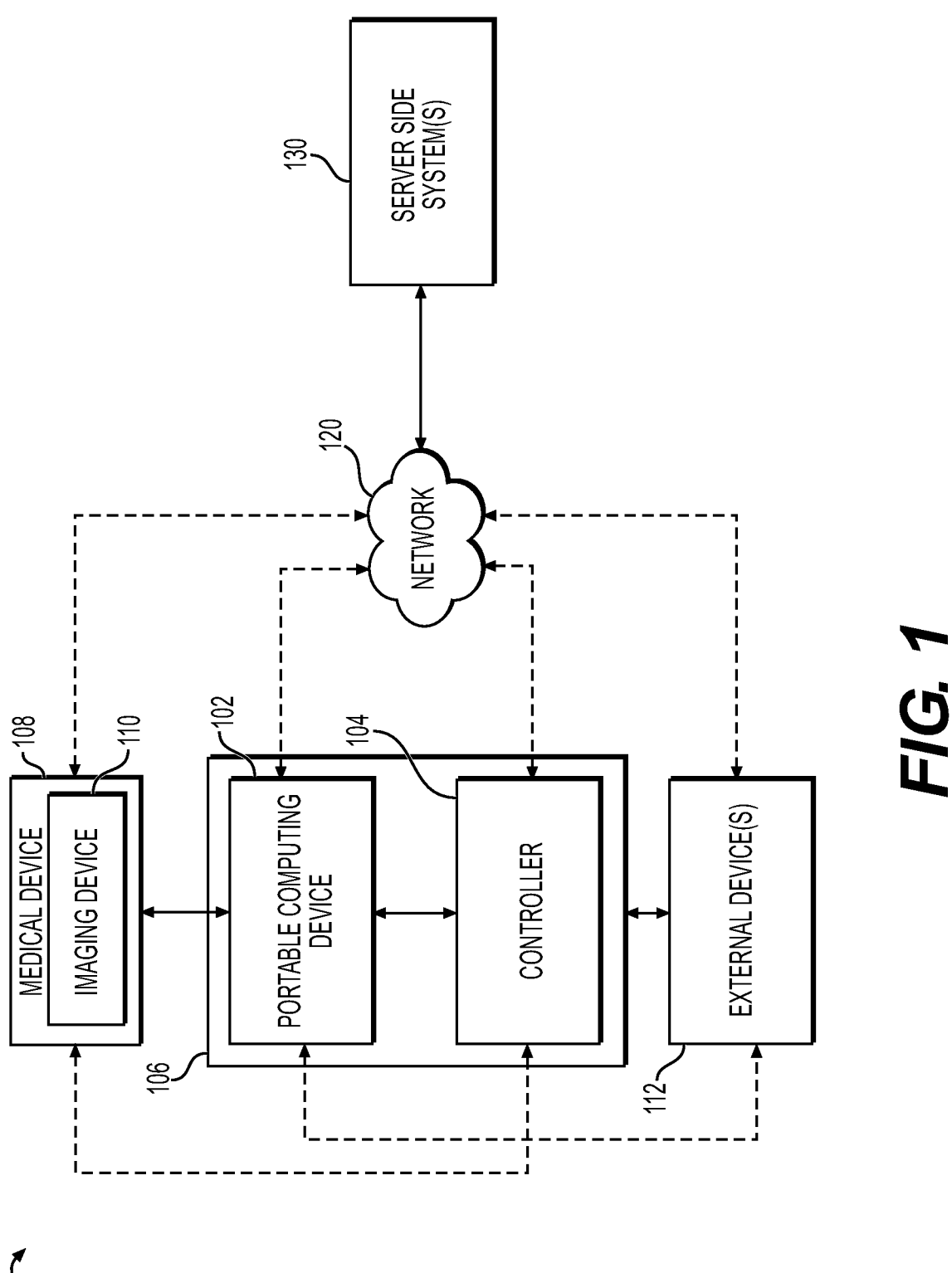
FIG. 1 depicts an exemplary medical imaging system.

As briefly discussed in the background, endoscopic procedures often are performed in one of two clinical settings. Resultantly, two types of conventional endoscopic imaging systems have emerged that are commonly implemented to accommodate each clinical setting. That is, each system type commonly implemented may have advantages or benefits for the corresponding clinical setting.

As one example, in the first clinical setting where the endoscopic procedure is performed in a dedicated area or room of a healthcare facility, such as an endoscopy suite, a first conventional endoscopic imaging system may be utilized. In the first conventional endoscopic imaging system, an endoscope may be connected to a dedicated controller.

One or more external display devices may also be set up at various locations in the dedicated area or room and connected to the dedicated controller. The dedicated controller may be configured to perform advanced image processing techniques to process image signals received from the endoscope to generate and display image data via the external display devices, for example. The dedicated controller may require a substantial amount of power at run time to execute the advanced image processing techniques. Therefore, the dedicated controller may be relatively fixed or stationary, such that the dedicated controller may be connected by a wired connection to an electric supply of the facility.

As another example, in the second clinical setting, where the endoscopic procedure is performed bedside, a second conventional endoscopic imaging system may be utilized that is more portable than the first conventional endoscopic imaging system. For example, the endoscope may be connected to a portable computing device, such as tablet, that is capable of performing image processing to generate and/or display image data based on image signals received from the endoscope. Due to the portability and corresponding battery limitations of the portable computing device, the image processing may be less advanced than the image processing performed by the dedicated controller in the first conventional type of endoscopic imaging system. However, in a bedside clinical setting, the portability may be critical (e.g., the portability benefits may outweigh less advanced image processing) given the limited space available for healthcare personnel and any medical equipment to be operated by the healthcare personnel during the procedure. In some examples, bedside procedures may be performed for emergent procedures and/or when patient isolation is deemed necessary (e.g., to prevent the transmission of infectious agents).

Aspects of this disclosure are directed to a medical imaging system that combines the benefits of both of the above-described conventional systems into a single system that may be utilized across different clinical settings. An exemplary medical imaging system may include both a portable computing device and a controller that each independently have image processing capabilities. A medical device, such as an endoscope, having an imaging device (e.g., on a distal end of an insertion portion of the endoscope) may be connected to the portable computing device. The portable computing device may be connectable to and disconnectable from the controller, and may operate in one of two modes based on the connection status.

For example, when the portable computing device is disconnected from the controller, the portable computing device may operate independently from the controller in a first operating mode. In the first operating mode, the portable computing device may be configured to process the image signals received from the imaging device to generate and display the image data via the portable computing device (e.g., the portable computing device serves as the image processing system similar to the second conventional imaging system). In the first operating mode, the portable computing device may also be configured to display a first user interface that, in addition to displaying the image data, includes a subset of imaging-related feature controls for operations that are enabled to be performed by the portable computing device.

When the portable computing device is connected to the controller, the portable computing device may operate in a second operating mode. In the second operating mode, the portable computing device may pass image signals from imaging device to the controller for processing to generate image data (e.g., the controller serves as the image processing system similar to the first conventional imaging system). Additionally, the portable computing device may provide a user interface for the controller (e.g., may display a second user interface) to enable user interaction with the imaging system. The second user interface may include a more extensive set of image processing-related feature controls than the first user interface based on the capability of the controller to perform additional imaging-related operations compared to portable computing device. In some examples, the second user interface may also optionally display image data generated by the controller. The image processing performed by the controller may be more advanced than imaging processing capable of being performed by the portable computing device, however the imaging system overall may be less portable. The controller may also provide additional memory for storage of image data, wired network connectivity, and/or connection to accessory devices, including external devices for triggering image capture by the imaging device.

Accordingly, aspects disclosed herein include a single medical imaging system that may be easily interchangeable to leverage benefits of advanced image processing versus enhanced portability dependent on a given clinical setting by connecting or disconnecting the portable computing device to or from the controller. Various configurations of the medical imaging system may be implemented. In one exemplary configuration, the controller may be a relatively fixed docking station to which portable computing device 102 docks to and undocks from to connect to or disconnect from the controller. In another exemplary configuration that provides further portability, the controller and a mount may each be mounted to a mobile stand. The portable computing device may dock to and undock from the mount to connect to or disconnect from the controller, and the mobile stand may be moved from one area to another within a healthcare facility.

FIG. 1 depicts an exemplary medical imaging system 100. Medical imaging system 100 may include two independent imaging processing systems, for example, a portable computing device 102 and a controller 104. Portable computing device 102 may be connectable to controller 104 to form a compound image processing system 106.

Portable computing device 102 may be any computing device capable of connecting to and disconnecting from controller 104. When disconnected from controller 104, portable computing device 102 may be highly portable and capable of independently operating as an image processing system. While portable computing device 102 is shown and described in examples herein as a tablet, portable computing device 102 is not limited to a tablet. In other examples, portable computing device 102 may be a laptop computer, a smart cellular phone, a personal digital assistant (PDA) device, etc. Controller 104 may be a dedicated image processing unit, a high power processing unit, a base station, a docking station, a supplemental computing device, etc. that is capable of operating as an image processing system. Specifically, controller 104 may be configured to perform advanced image processing techniques, such as artificial intelligence (AI)- or machine learning-based techniques, described in more detail elsewhere herein.

Figure 2B:
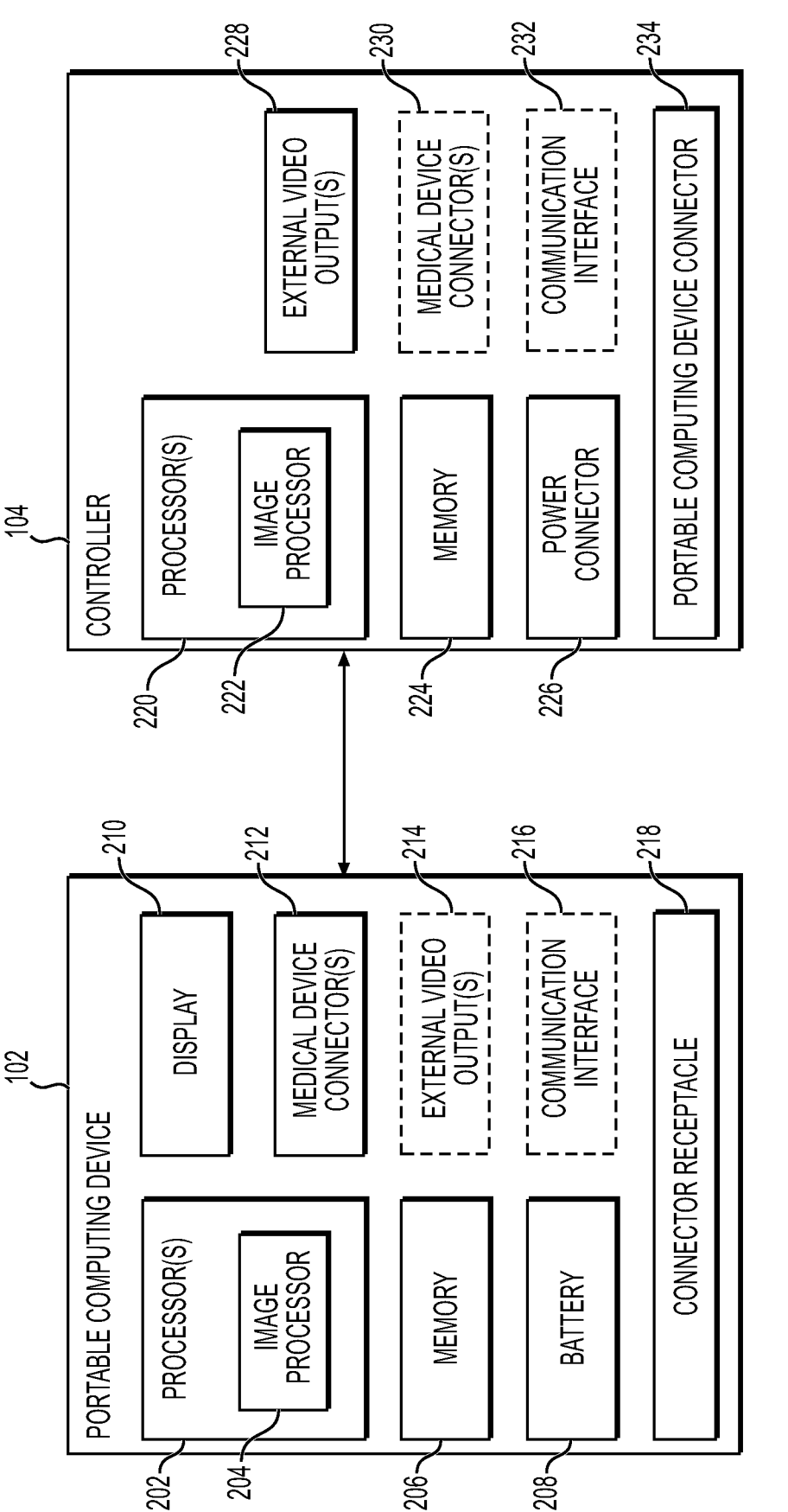
Figure 3A:
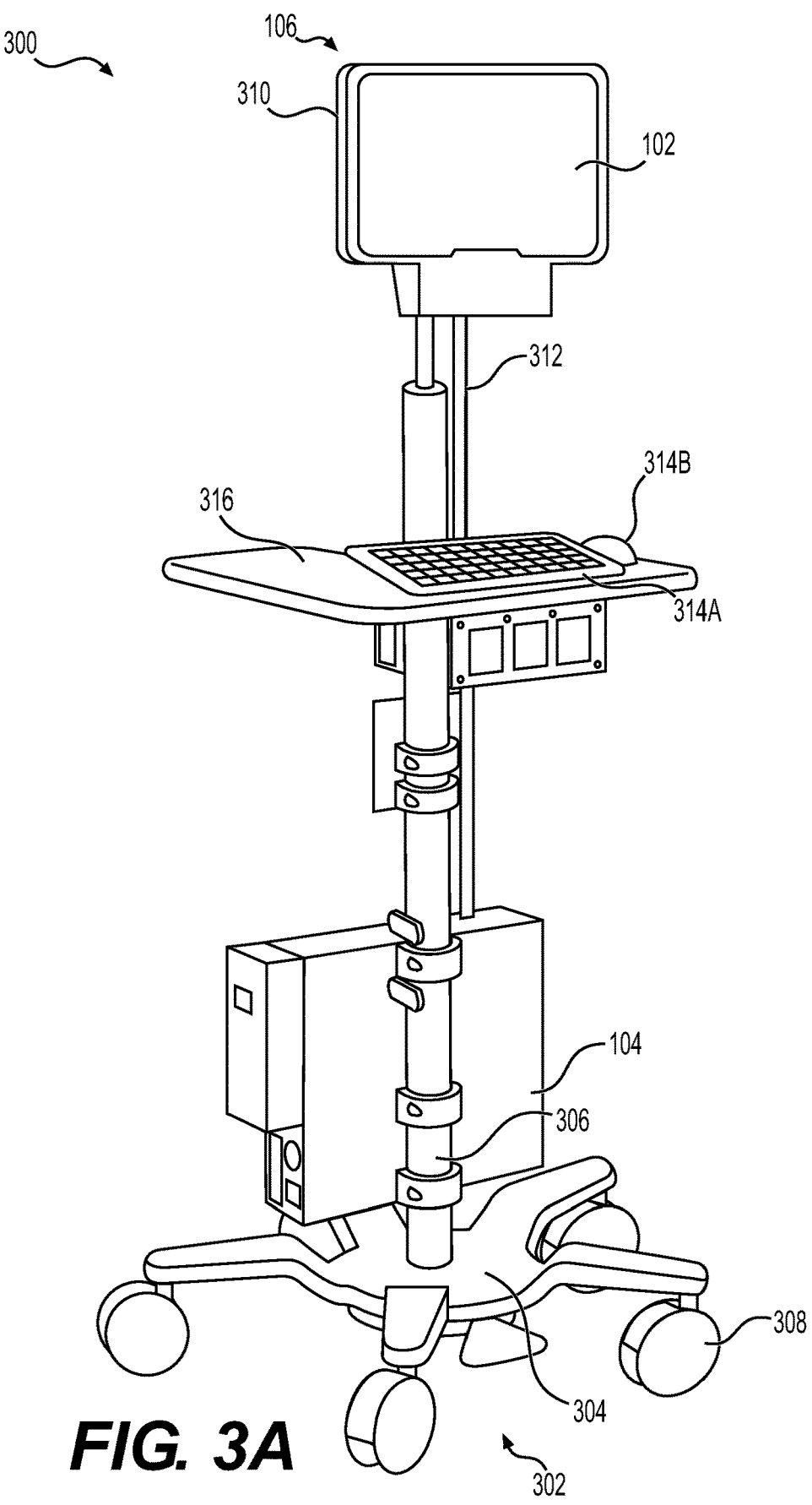
FIGS. 3A and 3B depict a second configuration of a portable computing device and a controller of the medical imaging system of FIG. 1.
Figure 3B:
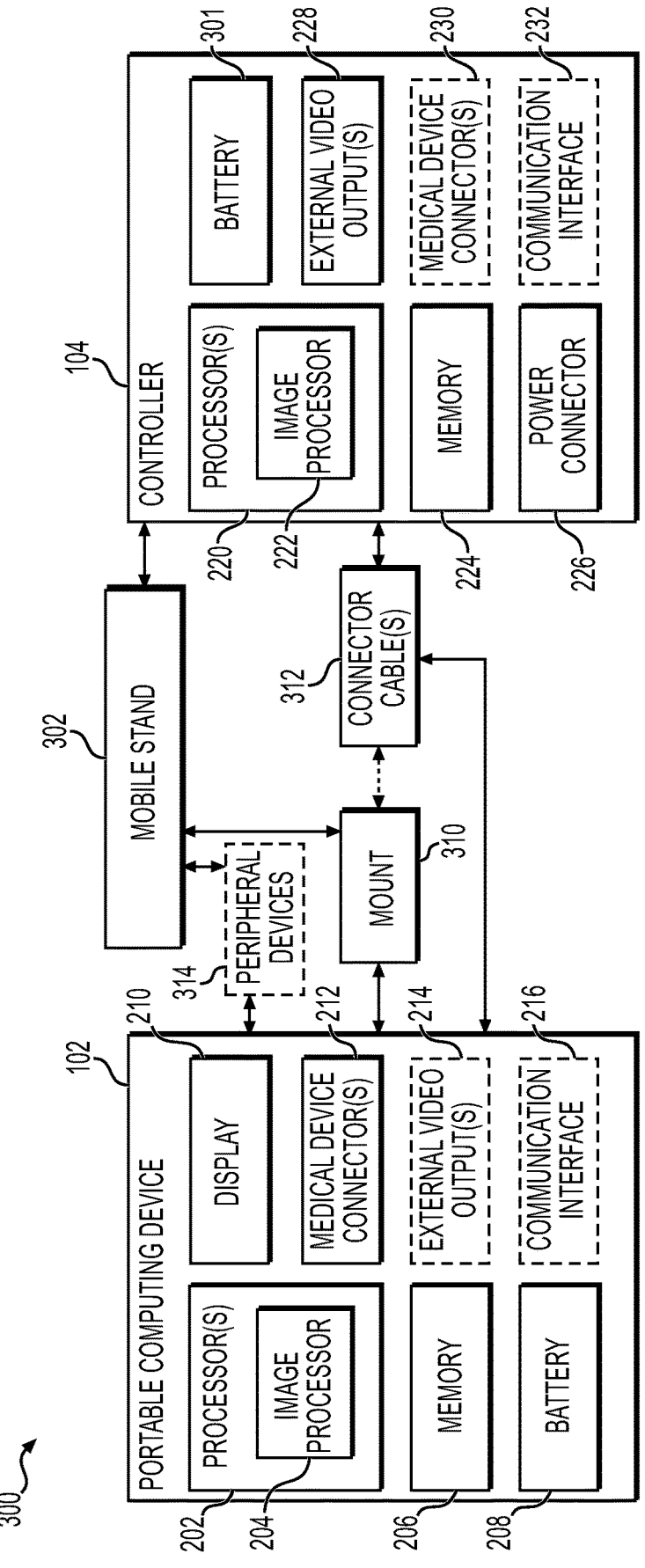

FIGS. 2A and 2B describe a first configuration of portable computing device 102 and controller 104, where controller 104 may be a docking station to which portable computing device 102 docks to (e.g., to form compound image processing system 106). FIGS. 3A and 3B describe a second configuration of portable computing device 102 and controller 104. In the second configuration, controller 104 may be mounted to a mobile stand, and the mobile stand may also include a mount to which portable computing device 102 may dock to. Docking portable computing device 102 to the mount may facilitate a connection between portable computing device 102 and controller 104 (e.g., to form compound image processing system 106). The first and second configurations are non-limiting and non-exhaustive configurations for portable computing device 102 and controller 104 of medical imaging system 100. Various other configurations may be implemented.

Medical imaging system 100 may also include a medical device 108. Medical device 108 may be used to perform a diagnostic and/or interventional procedure on a patient. Medical device 108 may be an endoscope or other type of scope, such as a bronchoscope, ureteroscope, duodenoscope, gastroscope, endoscopic ultrasonography ("EUS") scope, colonoscope, laparoscope, arthroscope, cystoscope, aspiration scope, sheath, or catheter, among other examples. Medical device 108 includes an imaging device 110 located at a distal end of medical device 108 (e.g., at a distal tip). Imaging device 110 may be configured to capture image signals as the distal end of medical device 108 is inserted into and navigated through a body lumen of the patient to a target site during the diagnostic and/or interventional medical procedure. Imaging device 110 may include one or more cameras, one or more image sensors, endoscopic viewing elements, or optical assemblies including one or more image sensors and one or more lenses, among other similar devices. Medical device 108 may also include one or more illumination devices (not shown). The illumination devices (e.g., one or more LEDs, optical fibers, and/or other illuminators) may be configured to illuminate areas of the patient's body (e.g., the target area) during the procedure to facilitate imaging by imaging device 110. In some examples, imaging device 110 and the illumination devices may form an imaging system.

Medical device 108 may be connected to portable computing device 102, such that image signals captured by imaging device 110 are received by portable computing device 102. For example, a connector plug extending from the proximal end of medical device 108 may connect medical device 108 to portable computing device 102. The connector plug may house one or more wires or cables connected to imaging device 110 to allow for delivery of the image signals captured by imaging device 110 to portable computing device 102. Dependent on an operating mode of portable computing device 102, portable computing device 102 may either operate as the image processing system to process the image signals to generate image data, or may operate as a translator to facilitate image processing performed by controller 104 to generate the image data (i.e., the controller 104 operates as the image processing system). Communication between portable computing device 102 and controller 104 may be agnostic to imaging device 110.

The operating mode of portable computing device 102 may be based on a connection status of portable computing device 102 and controller 104. If portable computing device 102 and controller 104 are not connected (e.g., there is a negative connection status indicated by a lack of physical and/or communicative connection), portable computing device 102 may operate in a first operating mode as the image processing system to generate and display image data. User interaction with the displayed image data may be enabled via a display 210 (FIG. 2B) of portable computing device 102. For example, portable computing device 102 may display a first user interface via display 210 (FIG. 2B) of portable computing device 102. The first user interface may include a subset of imaging-related feature controls selectable by the user for operations that are enabled to be performed by portable computing device 102. The first operating mode may be a default operating mode of portable computing device 102.

In some examples, portable computing device 102 and controller 104 may be intentionally disconnected based on a clinical setting that, for example, necessitates the portability enabled by portable computing device 102 when operated independently from controller 104. One such clinical setting may be a bedside procedure where available space is limited. In other examples, portable computing device 102 and controller 104 may be unintentionally disconnected. For example, portable computing device 102 may be improperly physically connected with controller 104 (e.g., a complete physical connection is not achieved), a communicative connection may not be established within a threshold period of time (e.g., a time out has occurred), and/or the communicative connection between portable computing device 102 and controller 104 may be sub-optimal (e.g., due to hardware issues or errors with controller 104).

Alternatively, if portable computing device 102 and controller 104 are connected to form compound image processing system 106 (e.g., there is a positive connection status indicated by a physical and/or communicative connection), portable computing device 102 may operate in a second operating mode as the translator, while controller 104 operates as the image processing system to generate image data. In some examples, compound image processing system 106 may be utilized in a clinical setting that, for example, provides for a dedicated area or room with sufficient space to house controller 104 and portable computing device 102 connected thereto. One such clinical setting may be a medical procedure performed in an endoscopy suite. As described in more detail below, the image data generated by controller 104 when portable computing device 102 is operated in the second operating mode may be displayed via one or more external displays set up in the dedicated area and/or may optionally be displayed by portable computing device 102.

When operating in the second operating mode, portable computing device 102 may provide a user interface for controller 104 to enable user interaction with controller 104. The user interface for controller 104 may be a second user interface displayed via display 210 (FIG. 2B) of portable computing device 102. The second user interface may include a more extensive (e.g., a full or complete) set of imaging-related feature controls as compared to the first user interface based on the capability of controller 104 to perform additional imaging-related operations than portable computing device 102. As one example, the second user interface may include control elements to allow a user to activate imaging device 110 to capture image signals and/or to record and save a still image and/or series of still images (e.g., a video) from the image data generated by controller 104. As another example, the second user interface may include control elements to manipulate (e.g., zoom in, zoom out, rotate, crop, increase brightness, decrease brightness, annotate, etc.) the image data generated by controller 104. As a further example, the second user interface may include control elements to power on and off the controller. In some examples, the second user interface may also optionally display image data generated by controller 104.

In other aspects, medical device 108 may optionally be connectable to controller 104. For example, the above-described connector plug extending from the proximal end of medical device 108 may connect medical device 108 to controller 104. That is, the connecter plug of medical device 108 may be interchangeably connected to either portable computing device 102 or controller 104. Accordingly, when portable computing device 102 is not connected to (e.g., is detached from) controller 104, medical device 108 may alternatively be connected to controller 104 via the connector plug. In such instances, controller 104 may be configured to receive and process image signals from imaging device 110 to generate image data.

Medical imaging system 100 may also include one or more external device(s) 112. At least one of external device(s) 112 may be a display device (e.g., a monitor, computing device screen, touch screen display device, etc.) connectable to controller 104, and configured to display image data generated by controller 104. External device(s) 112 may include one or more additional display devices that are connectable to controller 104. Optionally, external device(s) 112 may also include one or more display devices that are connectable to portable computing device 102, and configured to display image data generated by portable computing device 102 and/or controller 104. A particular one or more devices (e.g., portable computing device 102 and/or external device(s) 112) on which the image data is displayed may be based on the operating mode of portable computing device 102 and/or user-defined settings, as described in more detail below.

In some examples, external device(s) 112 may further include one or more third party processing systems, such as AI processing systems, connectable to controller 104 and/or portable computing device 102. Exemplary AI processing systems may be configured to receive the image data generated by controller 104 as an input and may also be configured to process the image (and optionally other input data) to generate augmented image data. In one example, the augmented image data may visually emphasize or highlight areas of interest, such as lesions, polyps, etc. In another example, the augmented image data may include an overlay representing a predicted position or trajectory of anatomical structures of interest that are currently obstructed or not visible in the image data due to other anatomical structures. In a further example, the augmented image data may include an overlay representing a predicted position and/or trajectory of a tool being delivered via medical device 108.

One or more components of medical imaging system 100, such as portable computing device 102, controller 104, medical device 108, and/or external device(s) 112, may be capable of network connectivity, and may communicate with one another over a wired or wireless network, such as a network 120. Network 120 may be an electronic network. Network 120 may include one or more wired and/or wireless networks, such as a wide area network ("WAN"), a local area network ("LAN"), personal area network ("PAN"), a cellular network (e.g., a 3G network, a 4G network, a 5G network, etc.), or the like. In one non-limiting, illustrative example, the components of medical imaging system 100 may communicate and/or connect to network 120 over universal serial bus (USB) or other similar local, low latency connections or direct wireless protocol.

In some embodiments, network 120 includes the Internet, and information and data provided between various systems occurs online. "Online" may mean connecting to or accessing source data or information from a location remote from other devices or networks coupled to the Internet. Alternatively, "online" may refer to connecting or accessing an electronic network (wired or wireless) via a mobile communications network or device. The Internet is a worldwide system of computer networks-a network of networks in which a party at one computer or other device connected to the network can obtain information from any other computer and communicate with parties of other computers or devices. Components of medical imaging system 100 may be connected via network 120, using one or more standard communication protocols, such that the component may transmit and receive communications from each other across network 120.

In some examples, when one or more of the components of medical imaging system 100 are capable of connecting to network 120, medical imaging system 100 may also include one or more server side system(s) 130. Server side system(s) 130 may include one or more of remote image processing systems configured to perform at least a portion of the image processing (e.g., to conserve local resources of portable computing device 102 and/or controller 104 when network connectivity is available). Additionally or alternatively, server side system(s) 130 may include data storage systems for storing the image data generated by portable computing device 102 and/or controller 104, and/or augmented image data generated by third party processing systems (e.g., one or more of external device(s) 112). In some examples, at least one of the data storage systems may include a picture archiving and communication system (PACS) that stores the image data and/or augmented image data, along with other types of imaging data from various imaging modalities (e.g., ultrasound, magnetic resonance, nuclear medicine imaging, positron emission tomography, computed tomography, mammograms, digital radiography, histopathology, etc.). Further, server side system(s) 130 may include endoscopic report writer systems configured to facilitate generation of a report based on the image data and/or augmented data.

Although various components in medical imaging system 100 are depicted as separate components in FIG. 1, it should be understood that a component or portion of a component in medical imaging system 100 may, in some embodiments, be integrated with or incorporated into one or more other components. In some embodiments, operations or aspects of one or more of the components discussed above may be distributed amongst one or more other components. Any suitable arrangement and/or integration of the various systems and devices of medical imaging system 100 may be used.

The specific examples included throughout the present disclosure implement medical imaging system 100 during a medical procedure performed in particular clinical settings (e.g., a dedicated area or room versus bedside). However, it should be understood that techniques according to this disclosure may be adapted to any clinical setting to leverage the advanced image processing benefits of compound image processing system 106 or the portability of portable computing device 102 disconnected from controller 104 to accommodate the particular clinical setting. It should also be understood that the examples above are illustrative only. The techniques and technologies of this disclosure may be adapted to any suitable activity.

FIG. 2A depicts a first configuration 200 of portable computing device 102 and controller 104. Controller 104 may be or otherwise include a docking station, and portable computing device 102 may dock to controller 104 (e.g., to form compound image processing system 106). In some examples, controller 104 may be a relatively fixed docking station that is positioned at a given location within a dedicated area or room of a healthcare facility, for example, in which procedures utilizing medical device 108 (FIG. 1) may be performed. As mentioned above, medical device 108 may be connected to portable computing device 102 to perform a procedure. Portable computing device 102 may be removed or undocked from controller 104 and operated independently if enhanced portability is needed for the procedure, for example. The docking and/or undocking of portable computing device 102 to and from controller 104 (e.g., a connection status) may be detectable by portable computing device 102 and cause portable computing device 102 to either operate in a first or second operating mode. Image processing of signals received by imaging device 110 of medical device 108 during the procedures may be dependent on the operating mode of portable computing device 102, as described below with respect to FIG. 2B.

FIG. 2B depicts a block diagram of components of each of portable computing device 102 and controller 104 in first configuration 200. As shown in FIG. 2B, portable computing device 102 may include one or more processor(s) 202, a memory 206, a battery 208, a display 210, one or more medical device connector(s) 212, and/or a connector receptacle 218, among other components. At least one of processor(s) 202 may include an image processor 204, such that portable computing device 102 has independent image processing capabilities. Portable computing device 102 may also optionally include one or more external video output(s) 214 for connecting to external device(s) 112 (FIG. 1) and/or a communication interface 216 for providing connectivity to network 120 (FIG. 1).

Controller 104 may include one or more processor(s) 220, a memory 224, a power connector 226, external video output(s) 228, and/or a portable computing device connector 234. At least one of processor(s) 220 may include an image processor 222. Controller 104 may optionally include one or more medical device connector(s) 230 for connecting to one or more medical devices, including medical device 108 (FIG. 1), for example, when medical device 108 is not otherwise connected to portable computing device 102. In some examples, if controller 104 includes multiple medical device connector(s) 230, multiple medical devices (e.g., of the same type or of varying types) may be connected in addition or alternatively to medical device 108 at a given time to perform a procedure. For example, in addition or alternatively to medical device 108, external imaging devices (e.g., X-ray devices, magnetic resonance imaging devices, etc.) may be connected to controller 104 via medical device connector(s) 230. Controller 104 may also optionally include a communication interface 232 for providing connectivity to network 120 (FIG. 1).

Referring first to portable computing device 102, memory 206 may store instructions to be executed by processor(s) 202 to cause portable computing device 102 to perform corresponding operations. Battery 208 may provide power to processor(s) 202 and/or one or more other components of portable computing device. Battery 208 may be rechargeable. In some examples, battery 208 may be automatically recharged when portable computing device 102 is docked to controller 104 (e.g., by an electric power supply accessed via power connector 226 of controller 104 described below). Additionally or alternatively, battery 208 may be recharged by connecting a battery charging cable from portable computing device 102 to an external power source (e.g., an electrical socket providing access to an electric power supply) and/or via wireless charging methods.

Medical device 108 may be connected to portable computing device 102 via medical device connector(s) 212. In some examples, if portable computing device 102 includes multiple medical device connector(s) 212, multiple medical devices (e.g., of the same type or of varying types) may be connected in addition or alternatively to medical device 108 at a given time to perform a procedure. For example, in addition or alternatively to medical device 108, external imaging devices (e.g., X-ray devices, magnetic resonance imaging devices, etc.) may be connected to portable computing device 202 via medical device connector(s) 212.

Image processor 204 of portable computing device 102 may be configured to process image signals to generate image data. In some examples, image processor 204 may be a basic field-programmable gate array (FPGA), a basic digital signal processing (DSP) processor, a graphics processing unit (GPU), or the like having run time power requirements that may be met by battery 208. That is, image processor 204 may be capable of performing basic image processing operations. Memory 206 may store instructions to cause image processor 204 to receive and process image signals from imaging device 110 of medical device 108 to generate image data when a first set of one or more conditions are met.

The first set of conditions may include medical device 108 being connected to portable computing device 102 via one of medical device connector(s) 212, and portable computing device 102 operating in the first operating mode. As described with reference to FIG. 1 and as described in further detail below, portable computing device 102 may operate in the first operating mode when portable computing device 102 is undocked from (e.g., lacks a physical connection to) controller 104 and/or is docked to but nonetheless lacks a communicative connection to controller 104.

One or more components of portable computing device 102 may generate, or may cause to be generated, one or more user interfaces based on instructions/information stored in memory 206, instructions/information received from the other components in medical imaging system 100, and/or the like. For example, portable computing device 102 may generate the first user interface and/or the second user interface based on the first or second operating mode of portable computing device 102, respectively. Moreover, one or more components of portable computing device 102 may cause the user interfaces to be displayed via display 210 of portable computing device 102 and/or via one or more other displays (e.g., external device(s) 112). The user interfaces may include the generated image data (e.g., still or live images), text, input text boxes, selection controls, and/or the like. A given display may include a touch screen or a display with other input devices or systems (e.g., a mouse, keyboard, etc.) for an operator to control the functions of portable computing device 102.

For example, display 210 may be a touch display, and an operator may interact with the image data displayed thereon via touch inputs (e.g., with the operator's finger(s)) or stylus inputs. In some examples, other input devices, such as a keyboard or mouse, may be connected to portable computing device 102 to facilitate operator interactions. Additionally or alternatively, if portable computing device 102 includes optional external video output(s), the image data may be provided for display to any external device(s) 112 connected to portable computing device 102 via external video output(s) 214. In further examples, if portable computing device 102 includes optional communication interface 216 providing network connectively, the image data may be provided over network 120 to one or more other components of medical imaging system 100, including server side system(s) 130 for further processing and/or storage, among other examples.

Additionally, memory 206 may store instructions to cause processor(s) 202 to instead translate image signals received from imaging device 110 into a standard protocol and transmit the standard protocol to controller 104 for processing when a second set of one or more conditions are met. The second set of conditions may include medical device 108 being connected to portable computing device 102 via one of medical device connector(s) 212 and portable computing device 102 operating in the second operating mode. As described with reference to FIG. 1 and as described in further detail below, portable computing device 102 may operate in the second operating mode when portable computing device 102 is docked to controller 104 (e.g., both physically and communicatively) to form compound image processing system 106. For example, the standard protocol may be transmitted from portable computing device 102 to controller 104 over a communication channel established when portable computing device 102 is docked to controller 104, discussed in detail below.

Now referring to controller 104, memory 224 may store instructions to be executed by processor(s) 220 to cause controller 104 to perform corresponding operations. Power connector 226 may couple controller 104 to an electric supply to provide power to processor(s) 220 and/or one or more other components of controller 104. For example, power connector 226 may connect to an electrical socket accessing electric power supply of a healthcare facility.

Image processor 222 of controller 104 may be configured to process image signals to generate image data. In some examples, image processor 222 may be an advanced field-programmable gate array (FPGA), an advanced digital signal processing (DSP) processor, or the like. Therefore, image processor 222 of controller 104 may be configured to perform advanced image processing (e.g., more complex image processing than image processor 204 of portable computing device 102). Exemplary advanced image processing techniques may include AI- or machine learning-based techniques that require more run time power. These advanced image processing techniques may be supported by direct connection of controller 104 to the healthcare facility's electric supply via power connector 226.

Memory 224 may store instructions to cause image processor 222 to receive and process image signals from imaging device 110 that have been translated into a standard protocol by portable computing device 102 to generate image data when a first set of one or more conditions are met. The first set of conditions may include medical device 108 being connected to portable computing device 102 via one of medical device connector(s) 212, and portable computing device 102 operating in the second operating mode, as described above. The generated image data may be provided to one or more of external device(s) 112 (FIG. 1) connected to controller 104 via corresponding external video output(s) 228 for display. In some examples, based on user-defined settings, the generated image data may additionally or alternatively be provided to portable computing device 102 via the connection created via connector receptacle 218 and portable computing device connector 234, discussed in detail below. The image data may then be displayed on portable computing device 102 (e.g., on display 210) and/or, if portable computing device 102 includes optional external video output(s) 214, to any external device(s) 112 connected to portable computing device 102 via external video output(s) 214.

One or more components of controller 104 may generate, or may cause to be generated, one or more user interfaces based on instructions/information stored in the memory 224, instructions/information received from the other components in medical imaging system 100, and/or the like. For example, in some instances, controller 104 may cause second interface to be generated by portable computing device 102 when portable computing device 102 is operating in the second operating mode. Moreover, one or more components of controller 104 may cause the user interfaces to be displayed via display 210 of portable computing device 102 and/or via one or more other displays (e.g., external device(s) 112). The user interfaces may include the generated image data (e.g., still or live images), text, input text boxes, selection controls, and/or the like. A given display may include a touch screen or a display with other input devices or systems (e.g., a mouse, keyboard, etc.) for an operator to control the functions of portable computing device 102 and/or controller 104.

Additionally, when controller 104 includes optional medical device connector(s) 230 via which medical device 108 is capable of connecting to controller 104 through, memory 224 may also store instructions to cause image processor 222 to receive and process image signals from imaging device 110 to generate image data when a second set of one or more conditions are met. The second set of conditions may include medical device 108 being connected to controller 104 via one of medical device connector(s) 230 (e.g., instead of portable computing device 102 which may or may not be docked to controller 104). Under such conditions, the generated image data may be provided for display to one or more external device(s) 112 connected to controller 104 via corresponding external video output(s) 228. Additionally or alternatively, if portable computing device 102 is docked to controller 104 and providing a user interface for controller 104 (e.g., the second user interface), the generated image data may be provided to portable computing device 102. The image data may then be displayed on portable computing device (e.g., on display 210) and/or, if portable computing device includes optional external video output(s) 214, to any external device(s) 112 connected to portable computing device 102 via external video output(s) 214.

In further examples, when either the first or second set of conditions are met, and controller 104 includes optional communication interface 232 providing network connectively, controller 104 may provide the image data over network 120 to one or more other components of medical imaging system 100. For example, controller 104 may provide the image data over network 120 to server side system(s) 130 for further processing and/or storage.

The docking or connection of portable computing device 102 and controller 104 in first configuration 200 may be based on a connection of connector receptacle 218 of portable computing device 102 and portable computing device connector 234 of controller 104. For example, connector receptacle 218 may be configured to receive portable computing device connector 234. In some examples, portable computing device connector 234 may be recessed within a docking bay formed in a housing of controller 104. The docking bay may help to support portable computing device 102 in a position that is readable, touchable, and/or otherwise ergonomic for an operator. Portable computing device connector 234 may include one or more optical fibers that support high resolution data transfer (e.g., high resolution image data) between portable computing device 102 and controller 104. Portable computing device connector 234 may also include one or more wires or cables for power transfer such that electric power may be supplied from controller 104 to recharge battery 208 of portable computing device 102 when portable computing device 102 is docked to controller 104 and controller 104 is connected via power connector 226 to an electric supply. However, as described above, portable computing device 102 may be also be rechargeable independent of docking to controller 104. In some examples, portable computing device connector 234 may further include additional wires or cables for transmitting other data types, such as patient information.

FIG. 2B depicts portable computing device 102 as including connector receptacle 218 and controller as including portable computing device connector 234. However, in other examples, controller 104 may include a connector receptacle that is configured to receive a controller connector of portable computing device 102.

FIG. 3A depicts a second configuration 300 of portable computing device 102 and controller 104. In second configuration 300, controller 104 and a mount 310 may each be mounted to or otherwise coupled to a mobile stand 302. Portable computing device 102 may dock to mount 310 in order to connect portable computing device 102 to controller 104 (e.g., to form compound image processing system 106). FIG. 3B depicts a block diagram of components included in second configuration 300.

Referring concurrently to FIGS. 3A and 3B, mobile stand 302 may include a base 304 configured to support a pole 306. Base 304 may include wheels 308 or other similar movement mechanisms to allow mobile stand 302 to be easily moved from one location to another within a healthcare facility (e.g., between designated areas or rooms, from designated areas or rooms to bedside, etc.).

Controller 104 may be mounted to base 304 and/or pole 306 to enable controller 104 to be moved as mobile stand 302 is moved (e.g., as opposed to a relatively fixed controller 104 as in first configuration 200). Controller 104 in second configuration 300 may include similar components as the controller 104 in first configuration 200. For example, controller 104 may include processor(s) 220, including image processor 222, memory 224, power connector 226, external video output(s) 228, optional medical device connector(s) 230, and optional communication interface 232, each described in detail with reference to FIG. 2B.

In second configuration 300, controller 104 may also include a battery 301. Battery 301 may be a more powerful battery than battery 208, for example, to support higher run time power requirements of image processor 222 (e.g., an advanced image processor). For example, battery 301 may be an uninterruptible power supply. Therefore, controller 104 and processor(s) 220 thereof may be continued to be powered by battery 301 even when power connector 226 is disconnected from the healthcare facility's electric power supply to, for example, move the mobile stand 302 from one location to another within the facility. Similarly, controller 104 and processor(s) 220 thereof may be continued to be powered by battery 301 when due to the clinical setting, for example, mobile stand 302 is not positioned close to an external electric supply. As shown in FIG. 3B, battery 301 is depicted as being an integral part of controller 104. However, in other examples, battery 301 may be a stand-alone component separate from and connectable controller 104.

Mount 310 to which portable computing device 102 may be docked or undocked may be configured to mount portable computing device 102 to pole 306 and otherwise provide structural support for portable computing device 102. A height and/or angle of mount 310 relative to pole 306 may be adjustable for increased ergonomics for the operator.

Portable computing device 102 in second configuration 300 may include similar components as portable computing device 102 in first configuration 200. For example, portable computing device 102 may include processor(s) 202, including image processor 204, memory 206, battery 208, display 210, medical device connector(s) 212, optional external video output(s) 214, and optional communication interface 216, each described in detail with reference to FIG. 2B.

One or more connector cable(s) 312 may connect controller 104 to portable computing device 102. For example, a first end of connector cable(s) 312 may be connected to controller 104. In some examples, the first end of connector cable(s) 312 may be fixed to controller 104. In other examples, the first end of connector cable(s) may be removable from controller 104. A second end of connector cable(s) 312 may be connected to and removed from portable device 102 to correspondingly connect and disconnect portable device 102 from controller 104.

In some aspects, connector cable(s) 312 may connect controller 104 to portable computing device 102 via mount 310 to, for example, enable one step docking and connection. For example, a second end of connector cable(s) may be received via an opening in mount 310 and secured to and/or within a housing of mount 310 using one or more fixation mechanisms (e.g., screws, plates, and/or pogo pins) such that the second end of connector cable(s) 312 may interface with and connect to portable computing device as portable computing device 10 is docked to mount 310. Resultantly, as portable computing device 102 is docked to mount 310 by operator, a connection may be concurrently established between portable computing device 102 and controller 104 (e.g., to form compound image processing system 106). Portable computing device 102 may then be removed or undocked from mount 310, and thus removed from the second end of connector cable(s) 312, to disconnect portable computing device 102 from controller 104 if enhanced portability is needed, for example. A manner in which the second end of connector cable(s) 312 are secured to and/or within the housing of mount 310 may facilitate a swift disconnection when portable computing device 102 is removed or undocked from mount 310.

The connection or disconnection of portable computing device 102 to and from controller 104 (e.g., a connection status) concurrently with the docking or undocking of portable computing device 102 to and from mount 310 may be detectable by portable computing device 102. The connection status detected may cause portable computing device 102 to either operate in a first or second operating mode. In some examples, mount 310 may include a mechanical feature (e.g., a switch), an electrical feature (e.g., an electrical contact), and/or an electronic detection feature that may facilitate detectability of the connection status by portable computing device 102.

In other aspects, connector cable(s) 312 may connect controller 104 directly to portable computing device 102 independent from mount 310. That is, docking and undocking of portable computing device 102 to and from mount 310 does not effect a connection status of portable computing device 102 and controller 104. Therefore, even if undocked from mount 310, portable computing device 102 may still be connected to controller 104 via connector cable(s) 312. Resultantly, operator may be given some addition mobility (e.g., a length of connector cable(s) 312) in which to handle portable computing device 102 when undocked, while still leveraging benefits of connection to controller 104 to perform more advanced image processing, for example. In such aspects, the connection or disconnection of portable computing device 102 to and from controller 104 (e.g., a connection status) via connection or removal of connector cable(s) 312 to and from portable computing device 102 may be detectable by portable computing device 102. The detected connection status may cause portable computing device 102 to either operate in the first operating mode or the second operating mode.

Optionally, rather than the second end of connector cable(s) 312 connecting to portable computing device via mount 310 or independent of mount 310, the second end of connector cable(s) 312 may connect to mount 310 itself. When portable computing device 110 is docked to mount 310, mount 310 may provide the connection between portable computing device 102 and controller 104. When portable computing device 102 is undocked, the connection may be broken.

Connector cable(s) 312 may include similar features and/or functionalities of portable computing device connector 234 in first configuration 200. For example, connector cable(s) 312 may include one or more optical fibers that support high resolution data transfer (e.g., high resolution image data) between portable computing device 102 and controller 104. Connector cable(s) 312 may also include one or more wires or cables for power transfer. For example, electric power may be supplied from controller 104 to portable computing device 102 via the power transfer cables to recharge battery 208 when portable computing device 102 is docked to controller 104, and controller 104 is connected via power connector 226 to an electric supply. Alternatively, controller 104 may provide electric power from battery 301 if controller 104 is not connected to the electric supply via power connector 226. In other examples, portable computing device 102 may be charged by other means (e.g., via wireless charging). Further, connector cable(s) 312 may include one or more wires or cables for transmitting standard image or video data (also referred to as standard video cables). Standard video cables may enable the use of standardized video display data for communication between portable computing device 102 and controller 104 when connected to form compound image processing system 106. Such use may also minimize a number of types of video output signals to be generated by controller 104 to output the generated image data to portable computing device 102 for display (e.g., on display 210) and other external display devices (e.g. from external device(s) 112) connected to controller 104.

In some examples, mount 310 may be configured to recharge battery 208 of portable computing device 102 independent of controller 104. That is, even if the controller 104 is powered off and/or not connected to an electric supply, mount 310 may be configured to recharge battery 208 when portable computing device 102 is docked to mount 310. In one example, when battery 301 is a stand-alone component separate from controller 104, mount 310 may be connected to and receive electric power supply from battery 301 for use in recharging battery 208 of portable computing device 102. In another example, mount 310 itself may include a battery (not shown) that provides electric power supply for recharging battery 208 of portable computing device.

Prior to or during a medical procedure, the connector plug extending from the proximal end of medical device 108 may be connected to portable computing device 102 via one of medical device connector(s) 212. A distal end of medical device 108 may be inserted into and navigated through a body lumen of the patient to a target site during the medical procedure. Imaging device 110 located at the distal end of medical device 108 may be configured to capture image signals as the medical device 108 is interested into and navigated through the body lumen to the target site. Portable computing device 102 may receive the image signals from imaging device 110.

Similar to first configuration 200 described with reference to FIG. 2B, operations performed by portable computing device 102 and/or controller 104 to process the image signals in second configuration 300 may be dependent on the operating mode of portable computing device 102. For example, if portable computing device 102 is not docked to mount 310 and/or is otherwise not connected to controller 104 via connector cable(s) 312, portable computing device 102 may operate in the first operating mode. Resultantly, in first operating mode, portable computing device 102 may be configured to process the image signals to generate and display the image data, as described in detail above with reference to FIG. 2B.

Alternatively, if portable computing device 102 is docked to mount 310 and/or is otherwise connected to controller 104 via connector cable(s) 312, portable computing device 102 may operate in second operating mode. Resultantly, in second operating mode, portable computing device 102 may be configured to translate the image signals to a standard protocol and transmit the standard protocol to controller 104 for processing. Image processor 222 of controller 104 may then be configured to receive and process the standard protocol to generate and provide the image data for display, as described in detail above with reference to FIG. 2B.

In the second operating mode, portable computing device 102 may also be configured to provide a user interface for controller 104 (e.g., generate and display a second user interface) to enable user interaction via display 210. Optionally, to further facilitate user interaction via the second user interface, one or more peripheral devices 314, such as a keyboard 314A, mouse 314B, or other similar input devices, may be indirectly connected to portable computing device 102 via mount 310 (or optionally directly connected to portable computing device 102 via a wired or wireless connection, such as a Bluetooth or other similar connection, over network 120). In other examples, peripheral devices 314 may be connected to controller 104 instead of portable computing device 102 and/or mount 310. Peripheral devices 314 may be supported by a tray 316 or other similar support structure that is mounted to pole 306 of mobile stand 302. A height and/or angle of tray 316 relative to pole 306 may be adjustable for increased ergonomics for the operator.

In other examples, controller 104 may include optional medical device connector(s) 230, and prior to or during a medical procedure, the connector plug extending from the proximal end of medical device 108 may be connected to controller 104 via one of medical device connector(s) 230. In such examples, image processor 222 may receive and process the image signals from imaging device 110 (e.g., directly from medical device 108 and not through portable computing device 102) to generate and provide image data for display, as described in detail above with reference to FIG. 2B.

FIG. 4 depicts an exemplary process 400 for processing image signals received from imaging device 110. In some examples, steps of process 400 may be performed by portable computing device 102 and/or controller 104.

At step 402, a connection status of portable computing device 102 and controller 104 may be determined. As described in more detail with reference to FIG. 5, the determination may be a two-step process to evaluate a physical connection and, if there is a physical connection, a communicative connection of portable computing device 102 and controller 104. The connection status may be determined to be a negative connection status if there is no physical connection and/or if there is no (or sub-optimal) communicative connection despite a physical connection. The connection status may be determined to be a positive connection status if there is both a physical connection and a sufficient communicative connection (e.g., a communicative connection that meets a communicative connectivity threshold). The connection status may be determined periodically and/or in response to detecting triggering events, as discussed in detail below with reference to FIG. 5.

At step 404, portable computing device 102 may be operated in a first operating mode or a second operating mode based on the connection status determined at step 402. For example, when the connection status determined at step 402 is a negative connection status, portable computing device 102 may be operated in the first operating mode. Alternatively, when the connection status determined at step 402 is a positive connection status, portable computing device 102 may be operated in the second operating mode.

The first operating mode may be a default operating mode in which the portable computing device 102 operates independently from controller 104 to act as an image processing system to perform image processing operations and display image data via a first user interface on display 210 (and/or optionally other display devices connected to portable computing device 102). In the second operating mode, portable computing device 102 may operate in conjunction with controller 104 to form compound image processing system 106. For example, when in the second operating mode, portable computing device 102 may provide a user interface for controller 104 (e.g., display a second user interface on display 210), and may act as an image signal translator to facilitate image processing operations performed by controller 104, as described in greater detail below with reference to FIG. 6.

At step 406, image signals may be received from imaging device 110. As discussed above in detail with reference to FIG. 1, imaging device 110 may be an imaging device of medical device 108 (e.g., a camera of an endoscope). Moreover, imaging device 110 may be configured to capture a plurality of images of a body lumen as medical device 108 is inserted into and navigated through the body lumen to a target site during a diagnostic and/or interventional procedure.

At step 408, based on the first or second operating mode of portable computing device 102, one or more of portable computing device 102 or controller 104 may process the image signals to generate image data. For example, and as described in more detail with reference to FIG. 6, when portable computing device 102 is operating in the first operating mode, image processor 204 of portable computing device 102 may perform the image processing of the image signals to generate image data. Alternatively, when portable computing device 102 is operating in the second operating mode, portable computing device 102 may serve as an image signal translator to initially process (e.g., translate) the image signals into standard protocol, and image processor 222 of controller may receive the standard protocol and perform the image processing to generate the image data. Image processor 222 may be configured to perform more advanced image processing techniques, such as AI- or machine learning-based image processing techniques, than image processor 204.

Additionally, in some examples, one or more of external device(s) 112 connected to portable computing device 102 and/or controller 104 may include one or more third party processing systems, such as AI processing systems. The third party processing systems may be configured to receive the image data generated by portable computing device 102 and/or controller 104, respectively, as input to generate augmented image data. The augmented image data may then be provided back to portable computing device 102 and/or controller 104, respectively, for display.

At step 410, the image data may be output for display on display 210 of portable computing device 102 or an external display device (e.g., one of external device(s) 112). A device on which the image data is displayed may be based on the operating mode of portable computing device 102 and/or user-defined settings.

For example, when portable computing device 102 is operating in the first operating mode, the image data generated by portable computing device 102 may be displayed on display 210 of portable computing device 102 and/or one or more display devices from external device(s) 112 connected to portable computing device 102 via external video output(s) 214. In one example, user-defined settings may indicate to display the image data on display 210 unless an external display device is detected as being connected to portable computing device 102. If an external display device is detected as being connected to portable computing device 102, the image data is to be diverted to the external display device for display (e.g., as long as characteristics and/or features of the external display device meets minimum display requirements). In another example, the user-defined settings may indicate to display the image data on display 210, and duplicate the display of the image data on an external display device detected as being connected to portable computing device 102. When more than one external display device is detected as being connected to portable computing device 102, one or more hierarchical rules may be optionally defined in the user settings to indicate which one or more of the external display devices to provide the image data to for display. In some examples, the rules may be based on characteristics or features of the external display devices to provide an optimal display of the image data. Additionally or alternatively, the rules may be based on the type and/or number of different types of data being displayed (e.g., still images and/or live images).

Alternatively, when portable computing device 102 is operating in the second operating mode and dependent on the user-defined settings, the image data may be displayed on one or more display devices from external device(s) 112 connected to controller 104 via external video output(s) 228, display 210 of portable computing device 102, and/or one or more display devices from external device(s) 112 connected to portable computing device 102 via external video output(s) 214. In one example, the user-defined settings may indicate to display the image data on the external display devices connected to controller 104 unless no such connections are detected, at which point the image data is to be displayed on display 210 of portable computing device 102 and/or external display devices, if any, connected to portable computing device 102. As another example, the user-defined settings may indicate to duplicate the display of the image data on the external display devices connected to controller 104 and the display 210 of portable computing device 102 and/or external display devices, if any, connected to portable computing device 102. As previously discussed above, one or more hierarchical rules may optionally be defined in the user settings to determine which one or more of the available display devices to provide the image data to for display.

Accordingly, certain embodiments may be performed for processing image signals received from imaging device 110. Process 400 described above is provided merely as an example, and may include additional, fewer, different, or differently arranged steps than depicted in FIG. 4.

Figure 5:
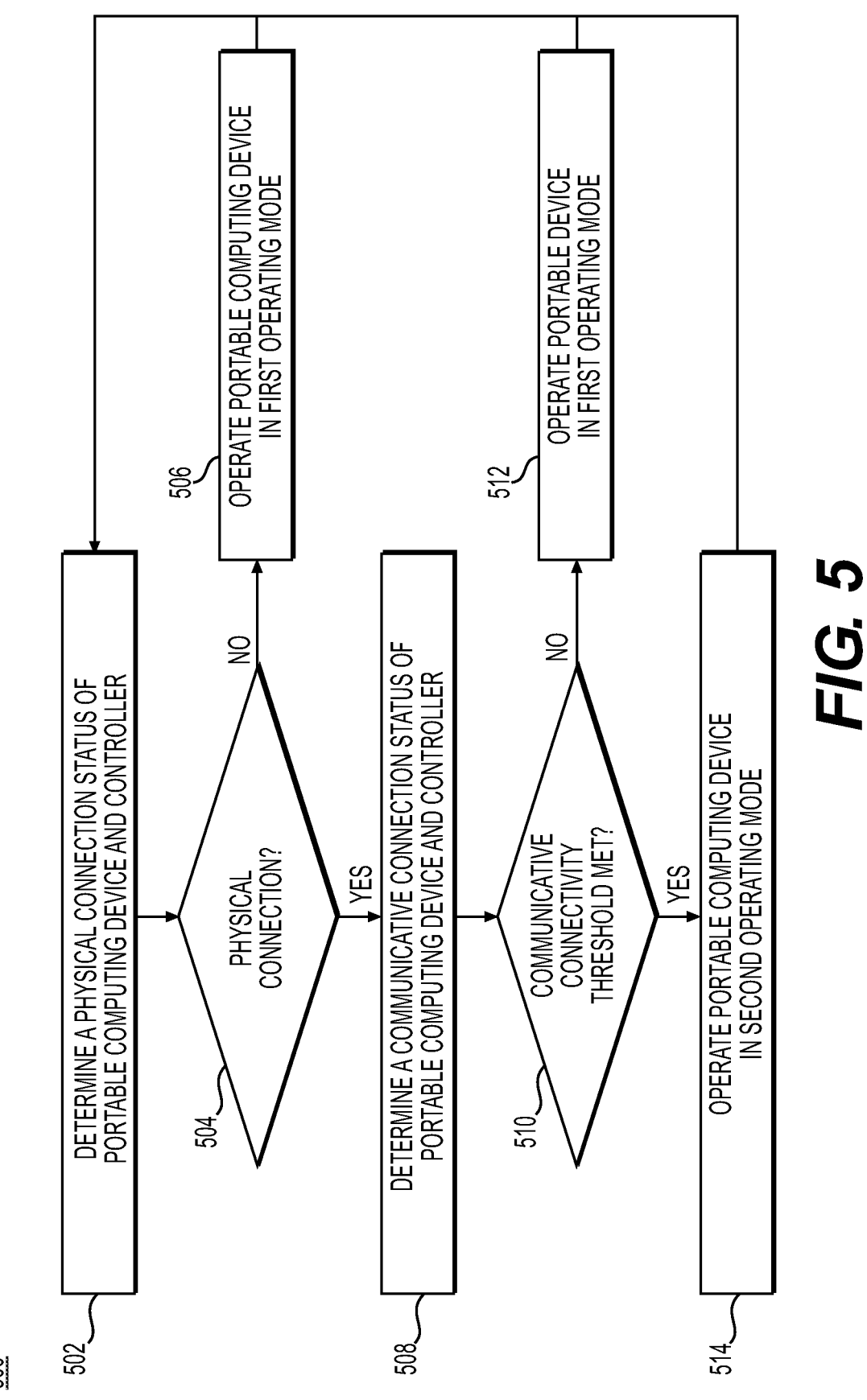
FIG. 5 depicts an exemplary process for determining a connection status of a portable computing device and a controller.

FIG. 5 depicts an exemplary process 500 for determining a connection status of portable computing device 102 and controller 104. In some examples, process 500 may be performed by portable computing device 102. Process 500 may be used to perform at least a portion of step 402 of process 400 described above with reference to FIG. 4.

At step 502, a physical connection status of portable computing device 102 and controller 104 may be determined. In some examples, a method for determining the physical connection status may be dependent on a configuration of portable computing device 102 and controller 104 (e.g., first configuration 200 or second configuration 300).

If in first configuration 200 as described with reference to FIGS. 2A and 2B, a positive physical connection status may be determined in response to connector receptacle 218 of portable computing device 102 having received portable computing device connector 234 of controller 104. Otherwise, a negative physical connection status may be determined. If in second configuration 300 as described with reference to FIGS. 3A and 3B, a positive physical connection status may be determined when a second end of connector cable(s) 312 is connected to portable computing device 102 via mount 310 and/or independent of mount 310 (the first end of connector cable(s) 312 being connected to controller 104). Alternatively, if in second configuration 300 second end of connector cable(s) 312 are instead connected to mount 310, a positive physical connection status may be determined in response to portable computing device 102 being docked to mount 310. Otherwise, a negative physical connection status may be determined.

At step 504, a decision of whether there is a physical connection of portable computing device 102 and controller 104 may be made based on the determined physical connection status. If the physical connection status is a negative physical connection status, there may be no physical connection, and process 500 may proceed to step 506. At step 506, portable computing device 102 may be operated in the first operating mode. Alternatively, if the physical connection status is a positive physical connection status, there may be a physical connection, and process 500 may proceed to step 508.

For other aspects, where a connection between portable computing device 102 and controller 104 is wireless (e.g., as opposed to wired via connector receptacle 218 and portable computing device connector 234 and/or via connector cable(s) 312)), process 500 may include alternative steps to steps 502 and 504. For example, instead of a physical connection status, a proximity status of portable computing device 102 and controller 104 may be determined. If portable computing device 102 and controller 104 are within a threshold range of proximity to enable communication, process may proceed to step 508. Alternatively, in the wireless context, process 500 may begin with step 508.

At step 508, a communicative connection status of portable computing device 102 and controller 104 may be determined. To determine the communicative connection status, a negotiation process (e.g., a handshake) between portable computing device 102 and controller 104 may be initiated by portable computing device 102. As part of the negotiation process, portable computing device 102 and controller 104 may exchange signals with one another to establish a communication link or channel. The signals may be exchanged via portable computing device connector 234, if portable computing device 102 and controller 104 are connectable in first configuration 200, or via connector cable(s) 312, if portable computing device 102 and controller 104 are connectable in second configuration 300. The exchanged signals may indicate to one another that each of portable computing device 102 and controller 104 is powered on and operable. Portable computing device 102 and controller 104 may also agree to the standard protocol (e.g., to which portable computing device 102 may translate the image signals to) and/or other associated parameters for transfer of data over the communication link through the exchanged signals during the negotiation process. Exemplary parameters may include information transfer rate, coding alphabet, parity, interrupt procedure, and/or other protocol or hardware features. In some examples, at least a portion of the parameters are to be agreed upon and/or meet a predefined minimum standard for a communicative connectivity threshold between portable computing device 102 and controller 104 to be met. Meeting the communicative connectivity threshold may help ensure that image signals (e.g., translated into standard protocol by portable computing device 102) may be effectively transmitted to controller 104 for processing by image processor 222. For example, to meet the communicative connectively threshold specific signals (e.g., synchronization signals) exchanged between portable computing device 102 and controller 104 may be detected at an expected time, meet minimum signal levels, etc.

In some examples, if there is an issue or error encountered during the negotiation process, the negotiation process may be re-initiated or retried. In other examples, the negotiation process may include a predefined timeout period. If a communicative connection is unable to be established within the predefined timeout period, then the negotiation process may fail causing the communicative connectivity threshold to not be met. In further examples, even if a communication link or channel is able to be established but the communication over the link or channel is sub-optimal for transmitting data over, the communicative connectivity threshold may not be met. In some examples, the sub-optimal communication may be due to hardware issues with controller 104.

At step 510, a decision of whether the communicative connectivity threshold between portable computing device 102 and controller 104 is met may be made based on the communicative connection status determined at step 508 (e.g., based on the negotiation process). If the communicative connectivity threshold is not met, process 500 may proceed to step 512. At step 512, portable computing device 102 may be operated in the first operating mode. If the communicative connectivity threshold is met, process 500 may proceed to step 514. At step 514, portable computing device 102 may be operated in the second operating mode.

In some examples, process 500 may be repeated periodically, for example, at predefined intervals. As one non-limiting example, process 500 may be repeated approximately every 0.25 seconds. In other examples, process 500 may be repeated in response to portable computing device 102 detecting a trigger event. One exemplary trigger event may include receiving of image signals from imaging device 110.

Dependent on the operating mode of portable computing device 102 when image signals are received from imaging device 110, different operations may be performed by portable computing device 102. The image processing operations performed by portable computing device 102 when operating in the first operating mode and translation operations performed by portable computing device 102 when operating in the second operating mode are described in detail with reference to FIG. 6 below.

Accordingly, certain embodiments may be performed for determining a connection status of portable computing device 102 and controller 104. Process 500 described above is provided merely as an example, and may include additional, fewer, different, or differently arranged steps than depicted in FIG. 5.

FIG. 6 depicts an exemplary process 600 for operating mode-dependent image processing. In some examples, process 600 may be performed by portable computing device 102. Process 600 may be used to perform at least a portion of steps 406, 408, and/or 410 of process 400 described with reference to FIG. 4.

At step 602, portable computing device 102 may receive image signals from imaging device 110. At step 604, process 600 may include determining whether portable computing device 102 is operating in the first or second operating mode, for example, as discussed above with respect to process 500 described with reference to FIG. 5. Based on whether portable computing device 102 is operating in the first or second operating mode, process 600 may either proceed to steps 606-608 when operating in the first operating mode, or to steps 610-612 and optionally step 614 when operating in the second operating mode.

When portable computing device 102 is operating in the first operating mode, at step 606, the image signals may be processed by image processor 204 of portable computing device 102 to generate image data. At 608, the image data may then be provided for display on display 210 of portable computing device 102 and/or on an external display (e.g., one of external device(s) 112) connected to portable computing device 102 via external video output(s) 214. In some examples, user settings may define which device is (or devices are) to display the image data.

When portable computing device 102 is operating in the second operating mode, at step 610, portable computing device 102 may translate the image signals to a standard protocol. The standard protocol may then be transmitted to controller 104 to be processed into image data at step 612. For example, image processor 222 of controller 104 may process the standard protocol to generate the image data. In some examples, image processor 222 may perform advanced image processing techniques, including AI- and/or machine learning-based image processing techniques, to generate the image data.

Once the image data is generated, controller 104 may provide the image data to one or more external device(s) 112 connected to controller 104 via external video output(s) 228. In some examples, the external device(s) 112 may include external display devices (e.g., monitors) configured to display the image data. In other examples, external device(s) 112 may include third party processing systems, such as AI processing systems, configured to receive the image data as input in order to generate augmented image data, for example. The controller may receive the augmented image data from the third party processing systems and provide the augmented image data for display.

Additionally or alternatively, controller 104 may optionally provide the image data (or augmented image data, if applicable) to portable computing device 102 for display. In such examples, at optional step 614, portable computing device 102 may receive the image data from controller 104 for display on display 210 of portable computing device 102 and/or an external display (e.g., one of external device(s) 112) connected to portable computing device 102 via external video output(s) 214.

Accordingly, certain embodiments may be performed for operating mode-dependent image processing. Process 600 described above is provided merely as an example, and may include additional, fewer, different, or differently arranged steps than depicted in FIG. 6.

Figure 7:
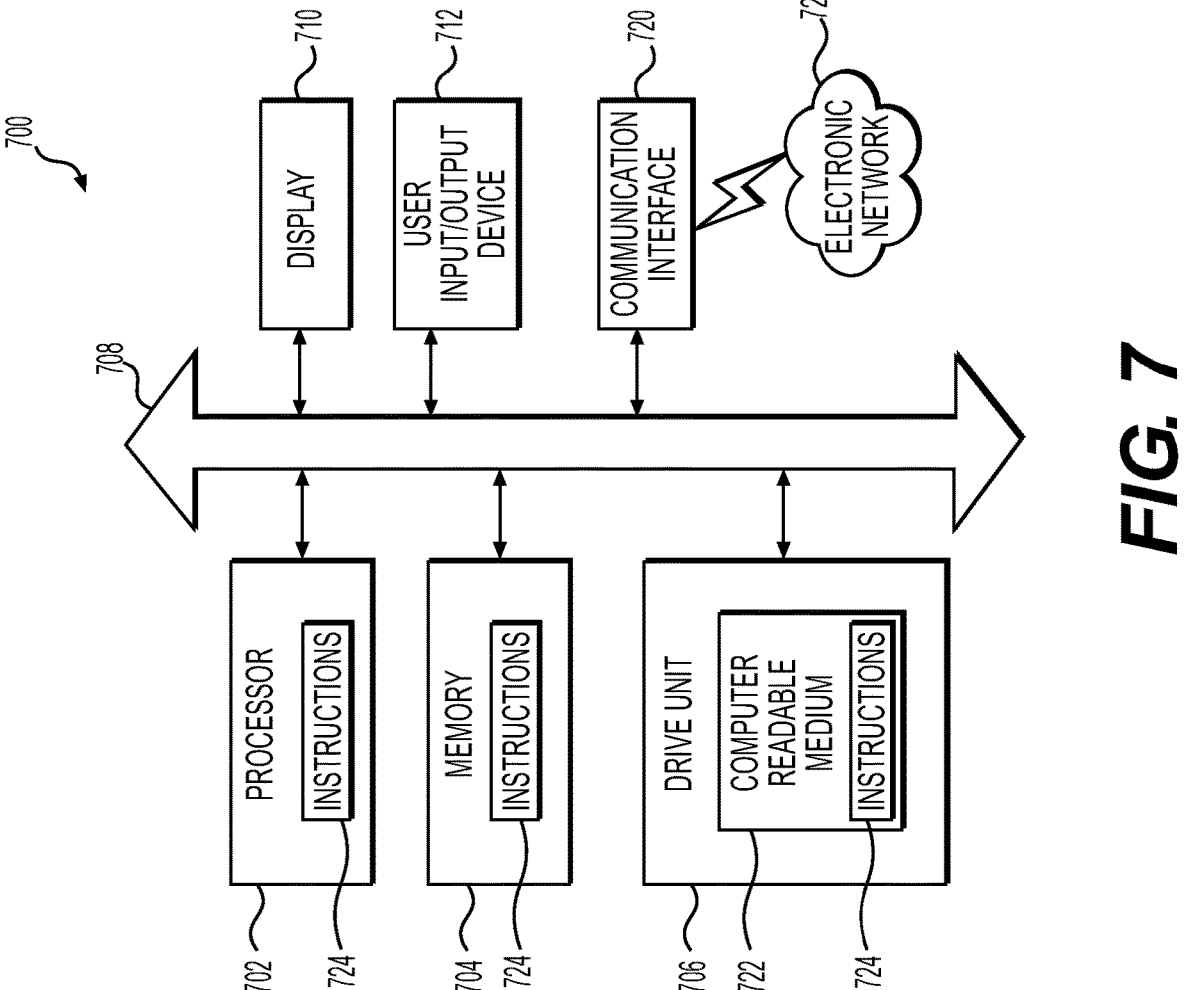
FIG. 7 depicts an example of a computing device.

FIG. 7 depicts an example of a computer 700. FIG. 7 is a simplified functional block diagram of computer 700 that may be configured as a device for executing processes, steps, or operations depicted in, or described with respect to, FIGS. 1-6 and, according to exemplary embodiments of the present disclosure. For example, computer 700 may be configured as one of portable computing device 102, controller 104, external device(s) 112, server side system(s) 130, and/or another device or component according to exemplary embodiments of this disclosure. In various embodiments, any of the systems herein may be or include computer 700 including, e.g., a data communication interface 720 for packet data communication. Computer 700 may communicate with one or more other computers, for example, using an electronic network 725 (e.g., via data communication interface 720). Electronic network 725 may include a wired or wireless network similar to network 120 depicted in FIG. 1.

Computer 700 also may include a central processing unit ("CPU"), in the form of one or more processors 702, for executing program instructions 724. Program instructions 724 may include instructions for running one or more applications or programs associated with determining a connection status, operating portable computing device 102 in a first or second operating mode, and performing corresponding basic image processing and/or translation operations based on the operating mode (e.g., if computer 700 is portable computing device 102). Program instructions 724 may include instructions for running image processing operations, including advancing image processing operations such as AI- or machine learning-based image processing (e.g., if computer 700 is controller 104 or one of server side system(s)).

Computer 700 may include an internal communication bus 708. Computer 700 may also include a drive unit 706 (such as read-only memory (ROM), hard disk drive (HDD), solid-state disk drive (SDD), etc.) that may store data on a computer readable medium 722 (e.g., a non-transitory computer readable medium), although computer 700 may receive programming and data via network communications. Computer 700 may also have a memory 704 (such as random-access memory (RAM)) storing instructions 724 for executing techniques presented herein. It is noted, however, that in some aspects, instructions 724 may be stored temporarily or permanently within other modules of computer 700 (e.g., processor 702 and/or computer readable medium 722). Computer 700 also may include user input and output devices 712 and/or a display 710 to connect with input and/or output devices such as keyboards, mice, touchscreens, monitors, displays, etc. The various system functions may be implemented in a distributed fashion on a number of similar platforms, to distribute the processing load. Alternatively, the systems may be implemented by appropriate programming of one computer hardware platform.

Program aspects of the technology may be thought of as "products" or "articles of manufacture" typically in the form of executable code and/or associated data that is carried on or embodied in a type of machine-readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may, at times, be communicated through the Internet or various other telecommunication networks. Such communications, e.g., may enable loading of the software from one computer or processor into another. Thus, another type of media that may bear the software elements includes optical, electrical, and electromagnetic waves, such as used across physical interfaces between local devices, through wired and optical landline networks and over various air-links. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

While principles of this disclosure are described herein with the reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:

1. A portable computing device of a medical imaging system connectable to a controller, the portable computing device comprising:

a medical device connector for connecting a medical device to the portable computing device, the medical device including an imaging device;

at least one memory storing instructions; and one or more processors, including an image processor, wherein execution of the instructions by the one or more processors, causes the portable computing device to perform operations, including:

determine a connection status of the portable computing device and the controller to one another;

based on the connection status of the portable computing device and the controller to one another, operate the portable computing device in a first operating mode or a second operating mode;

receive image signals from the imaging device;

when the portable computing device is operating in the first operating mode, process the image signals, by the image processor of the portable computing device, to generate image data; and when the portable computing device is operating in the second operating mode, provide the image signals to the controller for processing to generate the image data.

2. The portable computing device of claim 1, wherein, to determine the connection status, the operations include to:

determine a physical connection status of the portable computing device and the controller to one another; and in response to determining there is a physical connection of the portable computing device and the controller to one another based on the physical connection status, determine a communicative connection status of the portable computing device and the controller to one another.

3. The portable computing device of claim 2, wherein, when the physical connection status indicates there is no physical connection of the portable computing device and the controller to one another, the portable computing device is operated in the first operating mode.

4. The portable computing device of claim 2, wherein, to determine the communicative connection status, the operations include to initiate a negotiation process between the portable computing device and the controller to determine whether a communicative connectivity threshold is met.

5. The portable computing device of claim 4, wherein:

in response to determining that the communicative connectivity threshold is not met, the portable computing device is operated in the first operating mode; and in response to determining that the communicative connectivity threshold is met, the portable computing device is operated in the second operating mode.

6. The portable computing device of claim 1, wherein the connection status of the portable computing device and the controller to one another is periodically determined at predefined intervals.

7. The portable computing device of claim 1, wherein the connection status of the portable computing device and the controller to one another is determined in response to detecting a trigger event, and wherein at least one trigger event includes the receiving of the image signals from the imaging device.

8. The portable computing device of claim 1, wherein when the portable computing device is operating in the first operating mode, the operations further include one or more of:

display the generated image data on a display of the portable computing device, or provide the generated image data for display on an external display device connected to the portable computing device.

9. The portable computing device of claim 1, wherein:

when the portable computing device is operating in the first operating mode, the portable computing device provides a first user interface on a display of the portable computing device, the first user interface including a subset of a plurality of imaging-related feature controls corresponding to subset of a plurality of operations that are enabled to be performed by the portable computing device, and when the portable computing device is operating in the second operating mode, the portable computing device provides a second user interface on the display of the portable computing device, the second user interface including the plurality of imaging-related feature controls corresponding to the plurality of operations that are enabled to be performed by the controller.

10. The portable computing device of claim 1, wherein, when the portable computing device is operating in the second operating mode and the image signals are provided to the controller for processing to generate the image data, the operations further include:

translate the image signals to a standard protocol; and transmit the standard protocol to the controller to be processed.

11. The portable computing device of claim 1, wherein an image processor of the controller is configured to perform more advanced image processing than the image processor of the portable computing device.

12. The portable computing device of claim 1, wherein when the portable computing device is operating in the second operating mode, the operations further include:

receive the generated image data from the controller for display on one or more of a display of the portable computing device or an external display device connected to the portable computing device.

13. The portable computing device of claim 1, further comprising a connector receptacle configured to receive a connector of the controller to connect the portable computing device and the controller to one another.

14. The portable computing device of claim 1, wherein the portable computing device is configured to receive one or more connector cables that connect the portable computing device and the controller to one another.

15. The portable computing device of claim 14, wherein the one or more connector cables connect the portable computing device and the controller to one another via a mount configured to receive the portable computing device.

16. A system for medical image processing, the system comprising:

a controller having a first image processor; and a portable computing device connectable to the controller, the portable computing device comprising:

a medical device connector for connecting a medical device to the portable computing device, the medical device including an imaging device;

at least one memory storing instructions; and one or more processors, including a second image processor, wherein execution of the instructions by the one or more processors, causes the portable computing device to perform operations, including:

determining a connection status of the portable computing device to the controller;

based on the connection status of the portable computing device to the controller, operating the portable computing device in a first operating mode or a second operating mode, wherein the portable computing device is operated in the first operating mode based on a negative connection status and operated in the second operating mode based on a positive connection status;

receiving image signals from the imaging device of the medical device connected to the portable computing device via the medical device connector;

when the portable computing device is operating in the first operating mode, processing the image signals, by the second image processor of the portable computing device, to generate image data; and when the portable computing device is operating in the second operating mode, providing the image signals from the portable computing device to the controller for processing, by the first image processor of the controller, to generate the image data.

17. The system of claim 16, wherein providing the image signals from the portable computing device to the controller for processing includes:

translating the image signals to a standard protocol; and transmitting the standard protocol from the portable computing device to the controller for processing by the first image processor of the controller to generate the image data, wherein the first image processor of the controller is configured to perform more advanced image processing than the second image processor of the portable computing device.

18. The system of claim 16, wherein one of:

the controller is a docking station having a connector, and the portable computing device comprises a connector receptacle for receiving the connector to connect the portable computing device to the controller; or the controller and a mount for the portable computing device are mounted to a mobile stand, and one or more connector cables connect the portable computing device to the controller.

19. A method for medical image processing implemented by a portable computing device, the method comprising:

determining a connection status of the portable computing device having a first image processor to a controller having a second image processor, wherein an imaging device of a medical device is connected to the portable computing device;

based on the connection status of the portable computing device to the controller, operating the portable computing device in a first operating mode or a second operating mode, wherein the portable computing device is operated in the first operating mode based on a negative connection status and operated in the second operating mode based on a positive connection status;

receiving image signals from the imaging device;

when the portable computing device is operating in the first operating mode, performing a first image processing of the image signals, by the first image processor of the portable computing device, to generate image data; and when the portable computing device is operating in the second operating mode:

translating the image signals to a standard protocol; and transmitting the standard protocol to the controller for the controller to perform a second image processing, different from the first image processing, by the second image processor of the controller to generate the image data.

20. The method of claim 19, wherein determining the connection status comprises:

determining a physical connection status of the portable computing device to the controller; and in response to determining there is a physical connection of the portable computing device to the controller based on the physical connection status, determining a communicative connection status of the portable computing device to the controller.

* * * * *